United States Patent [19]

Aoyagi

[11] Patent Number: 4,474,797
[45] Date of Patent: Oct. 2, 1984

[54] FUNGICIDAL 1-METHYL-3,4-DIHALO-5-SUBSTITUTED-SULFONYLPYRAZOLES

[75] Inventor: Edward I. Aoyagi, Petaluma, Calif.

[73] Assignee: Chevron Research Company, San Francisco, Calif.

[21] Appl. No.: 499,570

[22] Filed: May 31, 1983

[51] Int. Cl.³ .................... C07D 231/18; A01N 43/56
[52] U.S. Cl. ................................ 424/273 P; 548/376
[58] Field of Search .................... 548/376; 424/273 P

[56] References Cited

U.S. PATENT DOCUMENTS 4,331,678  5/1982  De'Ath et al. ................. 424/273 P

OTHER PUBLICATIONS

Chem. Abst. 41, 4144d.

*Primary Examiner*—Henry R. Jiles
*Assistant Examiner*—Kurt G. Briscoe
*Attorney, Agent, or Firm*—S. R. LaPaglia; T. G. DeJohghe; S. L. Biggs

[57] ABSTRACT

Compounds of the formula:

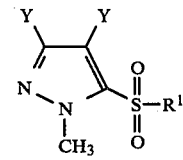

wherein $R^1$ is vinyl, 2-haloethyl or the group —$CH_2CH_2OS(O)_2CH_3$; and Y is chloro or bromo are fungicidal.

13 Claims, No Drawings

FUNGICIDAL 1-METHYL-3,4-DIHALO-5-SUBSTITUTED-SULFONYLPYRAZOLES

BACKGROUND OF THE INVENTION

This invention relates to certain novel pyrazole derivatives and their use as fungicides.

The 1-methyl-3,4,5-trihalopyrazole and 1-methyl-3,4-dihalo-5-(2-hydroxyethyl) pyrazole intermediates used in the preparation of these compounds, as well as processes for preparing them, are disclosed in my commonly-assigned pending U.S. patent application "Intermediates for 1-Methyl-3,4-Dihalo-5-Substituted Thio-, Sulfinyl-, or Sulfonyl-Pyrazole Fungicides", Ser. No. 393,214, filed June 28, 1982.

Fungicidal 1-methyl-3,4-dihalo-5-substituted thio-, sulfinyl-, or sulfonyl pyrazoles which have a

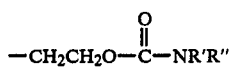

group attached to the 5-sulfur wherein R' and R'' are hydrogen, alkyl, cycloalkyl, lower alkenyl of 3 or more carbon atoms, alkylene carbalkoxy or aryl or aralkyl optionally substituted with 1 or 2 substituents, each independently selected from halogen, nitro, cyano, lower alkyl, lower alkoxy, trihalo-substituted methyl and phenoxy, are disclosed in my commonly assigned pending U.S. patent application "Fungicidal and Algicidal 1-Methyl-3,4-Dihalo-5-Substituted Thio-, Sulfoxyl- or Sulfonyl-Pyrazoles", Ser. No. 383,213, filed June 28, 1982.

Other fungicidal pyrazole derivatives are disclosed in my commonly assigned U.S. patent application "Fungicidal 1-Methyl-3,4-Dihalo-5-Alkylthiopyrazoles", Ser. No. 499,564, filed June 31, 1983.

SUMMARY OF THE INVENTION

The 1-methyl-3,4-dihalo-5-substituted-sulfonyl-pyrazole compounds of this invention are represented by the general formula:

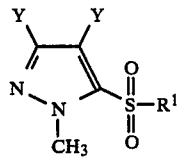

wherein $R^1$ is vinyl, 2-haloethyl or the group $-CH_2CH_2OS(O)_2CH_3$; and Y is chloro or bromo.

Among other factors, the present invention is based upon my finding that the 1-methyl-3,4-dihalo-5-substituted-sulfonylpyrazole compounds of the present invention are surprisingly effective as fungicides. In particular, these compounds seem surprisingly effective in inhibiting myceliar growth in fungi such as Rhizoctonia solani, Fusarium monilofroma, Botrytis cinerea and Aspargillos niger.

Definitions

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group $-(CH_2)_m-$ wherein m is an integer greater than zero. Typical alkylene groups include methylene, ethylene, propylene and the like.

The term "alkenyl" refers to unsaturated alkyl groups having a double bond [e.g., $CH_3CH=CH-(CH_2)_2-$] and includes both straight- and branched-chain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methyl-pent-4-enyl, and the like.

The term "halo" or "halogen" refers to the groups fluoro, chloro, bromo and iodo.

The term "pyrazole" refers to the

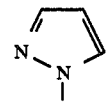

group. The conventional numbering system for this group is shown below:

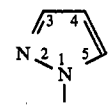

DETAILED DESCRIPTION OF THE INVENTION

The compounds of this invention may be prepared according to the following reaction sequences:

(a) The hydroxylethylthio intermediate is prepared according to the following reaction sequences:

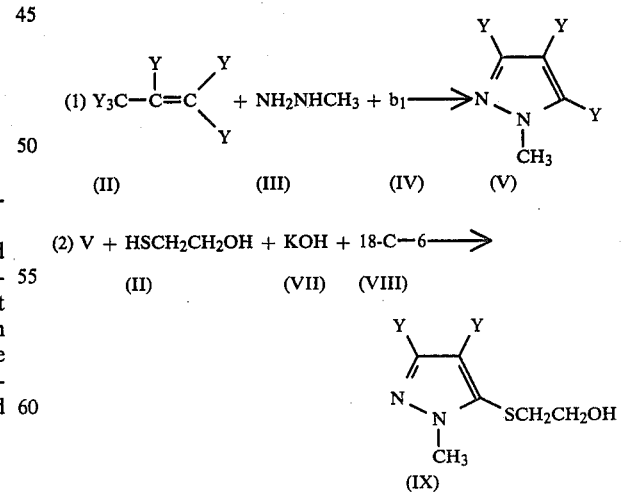

wherein Y is chloro or bromo, and $b_1$ is a base.

Reaction (1) is carried out by reacting (II) and (III) in the presence of base (IV). Suitable bases, $b_1$, include organic or inorganic bases, such as $K_2CO_3$, $Na_2CO_3$, triethylamine and the like. It is preferred to add an excess of (III) and (IV) per equivalent of (II) for ease of workup. It is especially preferred to add at least 3 and more preferably 5 equivalents of (IV) per equivalent of (II). Reaction (1) may be carried out by adding (IV) with stirring to a solution of (II) and solvent, followed by the slow addition of (III). For convenience, the reaction is carried out at ambient pressure. Suitable solvents include inert organic solvents such as toluene, benzene, dimethoxyethane, tetrahydrofuran and the like. The Product (V), a low-melting white solid, is isolated by conventional procedures such as extraction, chromatography, and recrystallization.

Reaction (2) is carried out by adding (V) to (VII) and (VI) in DMSO (dimethyl sulfoxide) and heating the resulting mixture for about 1 to about 24 hours. A catalytic amount of crown ether (18-crown-6) (VIII) may be used to facilitate the reaction. Reaction (2) may also be carried out in solvents such as DMF (dimethylformamide) and HMPA (hexamethylphosphoramide). Water is added to the reaction mixture, and Product (IX) is isolated by conventional techniques such as extraction, filtration, chromatography, or distillation.

Both compounds of formulas (V) and (IX) are disclosed in my commonly-assigned patent application "Intermediates for 1-methyl-3,4-dihalo-5-substituted thio-, sulfinyl- or sulfonyl-pyrazole fungicides".

(b) The compounds of formula I wherein $R^1$ is 2-haloethyl are prepared from the hydroxyethylthio intermediate IX according to the following reaction scheme:

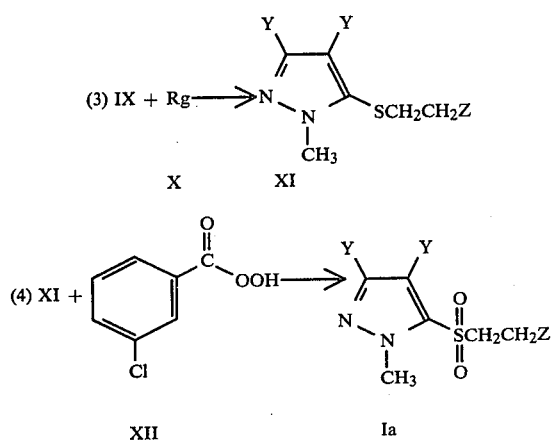

wherein Y is as previously defined, Z is halogen, and Rg is a reagent which substitutes a halogen for the hydroxyl group.

Reaction (3) is a conventional replacement reaction of the hydroxyl group with a halogen. Reaction (3) is carried out by combining IX and X in solvent. Although approximately equimolar amounts of IX and X may be used, it is preferred to use an excess of X. Reagent, Rg (X) is conventional reagent for the replacement of a hydroxyl group with a halogen. Suitable Rg's include thionyl chloride, hydrohalo acids, phosphorus trihalides, and the like. The choice of Rg will, to some extent, determine the exact reaction conditions. For example, where thionyl chloride is used, the reaction is conducted at a temperature of about 0° to about 100° C., preferably from about 35° to about 50° C. or at reflux; and is generally complete within about ½ to about 48 hours. Where Rg is phosphorus tribromide, the reaction is conducted at about 0° C. to about 100° C. or at reflux. With certain Rg's, including thionyl chloride and phosphorus tribromide, it may be preferred to add an amount of pyridine. For convenience, the reaction is carried out at ambient pressure. Suitable solvents include methylene chloride, benzene, chloroform, and the like. The product XI is isolated by conventional procedures such as stripping, extraction, washing, chromatography, and the like.

Reaction (4) is a selective oxidation of the thio group of XI to give the corresponding sulfonyl compound. Although meta-chloroperoxybenzoic acid (MCPBA) is the preferred oxidizing agent, other oxidizing agents may be used. Such suitable oxidizing agents include other peroxy acids such as peroxyacetic acid, or other reagents, including hydrogen peroxide in glacial acetic acid. Reaction (4) is conducted by adding XII to XI in solvent, preferably in portions. It is preferred to add 2 or more equivalents of XII per equivalent XI. The reaction is conducted at a temperature of about 0° to about 100° C., preferably about 20° to about 50° C. and generally is complete within about 1 to about 72 hours, or preferably the reaction mixture may be refluxed for about 2 to about 8 hours. For convenience, the reaction may be carried out at ambient temperature and pressure. Suitable solvents include chloroform, methylene chloride, other chlorinated hydrocarbon solvents, and the like. The product Ia is isolated by conventional methods such as filtration, washing, stripping, crystallization, and the like.

(c) The compounds of formula I where $R^1$ is vinyl are prepared according to the following reaction scheme:

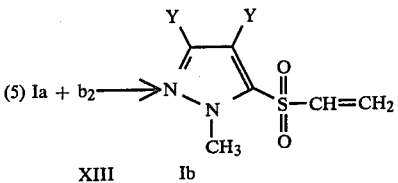

wherein Y is as previously defined and $b_2$ is a base.

Reaction (5) is conducted by combining Ia and XIII in solvent. Although the reactants may be combined in any order, it is preferred to add Ia to XIII in solvent. Suitable solvents include dimethoxyethane, methylene chloride, ether, tetrahydrofuran, and the like. Although equimolar amounts of Ia and XIII may be used, it is preferred to use a slight excess of XIII. Suitable bases, $b_2$, include organic and inorganic bases such as triethylamine, diazabicyclononane, DABCO, pyridine, potassium carbonate, sodium carbonate, and the like. The reaction is conducted at a temperature of about 0° to about 100° C., preferably from about 20° to about 85° C. or at reflux, and is generally complete within about 1 to about 5 hours. The product, Ib, is isolated by conventional procedures such as filtration, stripping, chromatography, crystallization, and the like.

(d) The compounds of formula I wherein $R^1$ is the group $-CH_2CH_2OS(O)_2CH_3$ are prepared from the hydroxyethylthio intermediate, IX, according to the following reaction scheme:

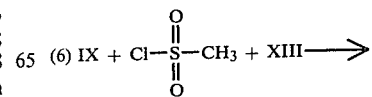

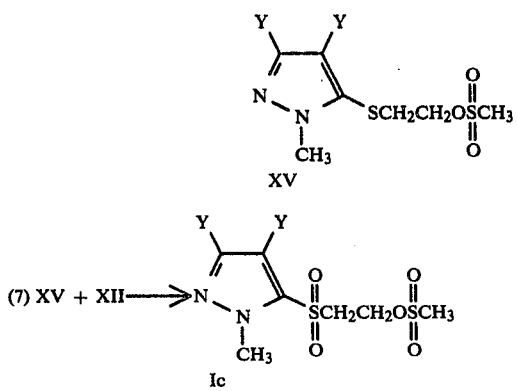

wherein Y is as previously defined.

Reaction (6) is conducted by combining IX, XIV and XIII in solvent. Suitable solvents include inert organic solvents such as methylene chloride, ethyl ether, chloroform, ethyl acetate, and the like. Although the reactants may be combined in any order, it is preferred to add XIII to a stirred mixture of IX and XIV in solvent. Approximately equimolar amounts of the reactants are used. Suitable bases include organic and inorganic bases such as triethylamine, diazabicyclononane, DABCO, pyridine, potassium carbonate, sodium carbonate, and the like. The reaction is conducted at a temperature of about 0° to about 100° C., preferably from about 20° to about 80° C. or, for convenience, at ambient temperature. The reaction is generally complete within about 1 to about 48 hours. The product XV is isolated by conventional procedures such as filtration, washing, stripping, chromatography, and the like.

Reaction (7) is an oxidation of a thio group to give the corresponding sulfone. Although meta-chloroperoxybenzoic acid (MCPBA) is the preferred oxidizing agent, other oxidizing agents may be used. Such suitable agents include other peroxy acids such as peroxyacetic acid, or other reagents, including hydrogen peroxide in glacial acetic acid. Reaction (7) is conducted by combining XV and XII in solvent. Suitable solvents include chloroform, methylene chloride, other chlorinated hydrocarbon solvents, and the like. Although the reactants may be combined in any order, it is preferred to add XII in portions to a stirred solution of XV in solvent. It is preferred to add at least 2 equivalents XII per equivalent XV. The reaction is conducted at a temperature of about 0° to about 100° C., preferably from about 20° to about 50° C., or for convenience at ambient temperature. The reaction is generally complete within about 1 to about 72 hours. The product Ic is isolated by conventional procedures such as washing, stripping, chromatography, crystallization, hard topping, and the like.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carriers, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

Many of the compounds of the invention are also useful for controlling microbiological organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, streams, canals, pools, and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep, 0.1 to 10 ppm is equal to about 0.3 to 30 pounds per acre of water one foot deep. These compounds may be applied to the aqueous growth environments of such organisms as dispersible powders or in solution with water-miscible solvents.

In addition, some of the compounds of the present invention exhibit herbicidal activity, generally in post-emergent applications. For post-emergent applications, the herbicidal compounds will be applied directly to the foliage and other plant parts. Generally, those compounds exhibiting herbicidal activity are effective against weed grasses as well as broad-leaved weeds. Some compound may be selective with respect to the type of application and/or type of weed.

A further understanding of my invention may be had from the following non-limiting examples.

EXAMPLES

Example 1

Preparation of 1-methyl-3,4,5-trichloropyrazole

To a rapidly stirred mixture of 11.4 g (0.046 mole) hexachloropropene and 16.6 g (0.12 mole) potassium carbonate in 100 ml toluene, 1.85 g (0.04 mole) methyl hydrazine was added slowly. The addition was slightly exothermic and the color of the reaction mixture turned to light orange-brown. The reaction mixture was then stirred overnight at ambient temperature. The reaction mixture was then heated to about 80° C. for about three hours and then cooled. A powdery solid appeared in the mixture. The mixture was filtered and the solids washed with ethyl ether.

The ethyl ether washings and reaction mixture filtrate were combined and stripped under reduced pressure and heat to give a black oil. The oil was chromatographed on a silica column, eluting first with hexane (which elutes unreacted starting materials) and then with methylene chloride. The methylene chloride eluate was stripped to give a pale yellow oil which solidified upon standing. Recrystallization from hexane gave 2.5 g of the product, a white solid with a melting point of 33°–35° C.

Elemental analysis for $C_4H_3Cl_3N_2$ showed: calculated %C 25.90, %H 1.63, and %N 15.11; found %C 23.67, %H 1.65, and %N 13.8.

By following the above procedure, but starting with 114 g (0.4 mole) of hexachloropropene and the corresponding proportions of the other reactants, 32.9 g of the product was prepared, a 34% yield (of theoretical).

Example 1A

Preparation of 1-methyl-3,4,5-trichloropyrazole

To a stirring solution of 250 g (1 mole) of hexachloropropene in 250 ml toluene, there was added 94.4 g (2.05 moles) of methyl hydrazine dropwise. The temperature of the reaction mixture was maintained in the range of about 50° to about 60° C. by the use of external cooling. When the addition of methyl hydrazine was complete, the reaction mixture was cooled to room temperature and 276 g (2 moles) of potassium carbonate was added. The resulting mixture was carefully heated first to about 60° C., then gradually to about 85° to 90° C. Heating was carefully monitored to control occasional exotherm and degassing. After about three hours, the heat source was removed and the reaction mixture was allowed to cool to room temperature. The reaction mixture was diluted with about 500 ml ice water and extracted with methylene chloride. The organic layer (containing the product) was washed twice with water, dried over magnesium sulfate and concentrated on a rotovac to give a red oil (about 275 ml). The red oil was dissolved in hexane and filtered through a short silica column twice to give 133 g of a yellow oil which solidified. Spectra of the solid were identical to those of the product of Example 1.

Example 2

Preparation of 1-methyl-3,4-dichloro-5-(2-hydroxyethylthio)pyrazole

To a mixture of 26.5 g (0.34 moles) 2-mercaptoethanol, 19 g of 85% potassium hydroxide, and a few drops of 18-Crown-6 in 250 ml of DMSO, 60 g (0.32 moles) 1-methyl-3,4,5-trichloropyrazole were added in portions. When the addition was complete, the reaction mixture was heated to 140° C. for 1 day. The cooled reaction mixture was diluted with water and extracted with ether. The organic phase was washed four times with 200 ml water per time, dried and stripped. The crude product was chromatographed on a silica gel column. The product, 1-methyl-3,4-dichloro-5-(2-hydroxyethylthio)pyrazole, was eluted from the column with ethyl acetate, yielding 27.7 g (37.7% yield) of a yellow oil.

Elemental analysis for $C_6H_8Cl_2N_2OS$ showed: calculated % C 31.73, % H 3.55, and % N 12.34; found % C 36.98, % H 3.77, and % N 12.60.

Example 3

Preparation of

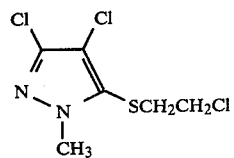

1-Methyl-3,4-dichloro-5-(2-chloroethylthio)pyrazole

To a stirred mixture of 48.4 g (0.213 moles) 1-methyl-3,4-dichloro-5-(2-hydroxyethylthio)pyrazole and 50 ml thionyl chloride in 200 ml methylene chloride, about 1 ml pyridine was added. The reaction mixture was heated at reflux for about 12 hours over 2 days time. The solvent was stripped, and the residue was taken up in ether. The etheral solution was washed 5 times with water and then dried over magnesium sulfate. Stripping of the ether gave 52.2 g of the product as a brown-red oil.

Example 4

Preparation of

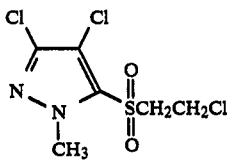

1-Methyl-3,4-dichloro-5-(2-chloroethylsulfonyl)-pyrazole

To a stirred solution of 52.2 g (0.212 moles) 1-methyl-3,4-dichloro-5-(2-chloroethylthio)pyrazole in 700 ml chloroform, 94.8 g (0.467 moles) of 85% meta-chloroperoxybenzoic acid were added in portions. The reaction mixture was stirred overnight at room temperature. The reaction mixture was then filtered and the solid was discarded. The filtrate was washed with a saturated sodium bicarbonate solution, and dried over magnesium sulfate. Stripping of the solvent gave an oil which crystallized on cooling with dry ice. Recrystallization from methylene chloride hexane using dry ice for cooling followed by filtering gave 39.2 g of the product as a white solid, melting point 56°–59° C. A second crop of about 4 g was also collected.

Elemental analysis for $C_6H_7Cl_3N_2SO_2$ showed: calculated %C 25.97, %H 2.54, and %N 10.10; found %C 27.1, %H 2.62, and %N 10.39.

Example 5

Preparation of

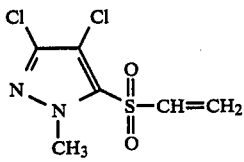

1-Methyl-3,4-dichloro-5-vinylsulfonylpyrazole

To a solution of 2.2 g (0.022 moles) triethylamine in 75 ml dimethoxyethane, 5 g (0.018 moles) 1-methyl-3,4-dichloro-5-(2-chloroethylsulfonyl)pyrazole were added. The reaction mixture was stirred at ambient temperature for about one hour and then heated to reflux and refluxed about 2 hours. The reaction mixture was filtered, and the filtrate was stripped to give a yellow oil. The oil was chromatographed on silica gel eluting with methylene chloride yielding a thick oil which crystallized upon cooling with dry ice. Recrystallization from methylene chloride-hexane gave the product as a white solid, melting point 66°–69° C.

Elemental analysis for $C_6H_6Cl_2N_2O_2S$ showed: calculated %C 29.86, %H 2.51, and %N 11.63; found %C 30.74, %H 2.61, and %N 11.85.

Example 6

Preparation of

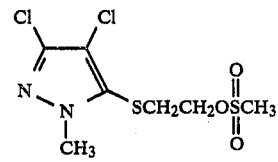

1-Methyl-3,4-dichloro-5-(2-methylsulfonyloxyethylthio)pyrazole

A solution of 5 g (0.022 moles) 1-methyl-3,4-dichloro-5-(2-hydroxyethylthio)pyrazole and 2.52 g (0.022 moles) methane sulfonyl chloride in 100 ml methylene chloride was stirred at room temperature for two days. To that mixture, 2.4 g (3.3 ml) triethylamine was added. The reaction mixture was then stirred over the weekend. The mixture was filtered and the filtrate was washed with water, then dried over magnesium sulfate, and then cooled with dry ice. Stripping of the solvent, followed by chromatography on silica gel, eluting with 5% ethyl acetate/methylene chloride gave 5.1 g of the product as a viscous yellow oil.

Elemental analysis for $C_7H_{10}Cl_2N_2O_3S_2$ showed: calculated %C 27.55, %H 3.30, and %N 9.18; found %C 27.9, %H 3.36, and %N 9.25.

Example 7

Preparation of

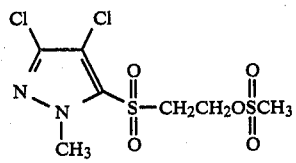

1-Methyl-3,4-dichloro-5-(2-methylsulfonxyoxyethylsulfonyl)pyrazole

To a stirred solution of 4.0 g (0.0131 moles) 1-methyl-3,4-dichloro-5-(2-methylsulfonyloxyethylthio)pyrazole (the product of Example 6) in 100 ml chloroform, 5.0 g of 80% meta-chloroperoxybenzoic acid were added in portions. The reaction mixture was stirred two days at room temperature. The reaction mixture was then washed twice with a saturated sodium bicarbonate solution and dried over magnesium sulfate. The solvent was stripped to give an oil which later crystallized. That residue was chromatographed on silica gel, eluting first with methylene chloride and then with 10% ethyl acetate/methylene chloride. The fractions containing the product were stripped and then hard topped to give a viscous oil which later crystallized, giving 2.3 g of a white solid.

Elemental Analysis for $C_7H_{10}Cl_2N_2O_5S_2$ showed: calculated %C 24.93, %H, 2.99, and %N 8.31; found %C 26.39, %H 2.96, and %N 8.35).

Compounds made according to Examples 1 to 7 are found in Table I.

Example A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

Example B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

Example C

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

Example D

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

Example E

Grape Downy Mildew

The compounds of this invention were tested for the control of the Grape Downy Mildew organism, *Plasmopara viticola*. Seedlings of *Vitis vinifera* var. Emperor (7+ weeks old) were used as hosts. The plants were sprayed with a 250 ppm solution of the test compound in an acetone and water solution containing a small amount of non-ionic emulsifier. The treated plants were inoculated one day later by spraying them with a spore suspension of the organism. The treated plants were then held in a greenhouse at a temperature of about 68° F. to about 72° F. (relative humidify varied between about 30 and about 99%) for 4 days. The plants were then placed in an environmental chamber at 100% relative humidity to induce sporulation. On removal from the chamber and after drying, the plants were evaluated for disease development. The percent disease control provided by a given test compound was based on the percent disease reduction relative to untreated check plants. The results are reported in Table II.

Example F

Bean Rust

The compounds of this invention were evaluated for their ability to eradicate Bean Rust caused by *Uromyces phaseoli tipica* on pinto beans.

Pinto bean plants, variety Idaho 1-11, 16 (summer) or 19 (winter) days old were inoculated with a 50-ppm suspension of uredospores in water containing a small amount of non-ionic surfactant. The inoculated plants were placed in an environmental chamber immediately after inoculation and incubated 20 hours. Following the incubation period, the plants were removed from the chamber and placed in a greenhouse maintained at 66°–68° F. and 60-80% relative humidity. Two days after inoculation, the plants were treated by spraying with a 250-ppm solution of test compound in an acetone and water carrier formulation containing a small amount of non-ionic surfactant. One or two replicate pots (each containing two plants) were used for each compound. In addition, one or two replicate pots were sprayed with the same carrier formulation (without a test compound) as a control (hereinafter "untreated Checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table II.

Example G

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table II.

Example H

Mycelial Inhibition

A number of the compounds of the present invention were evaluated for in vitro fungicidal effectiveness by means of a mycelial inhibition test. This test is designed to measure the fungitoxic activity of fungicidal chemicals in terms of their degree of inhibition of mycelium growth. Fungi used were *Phythium ultimum, Rhizoctonia solani, Fusarium monilofroma, Botrytis cinerea* and *Aspargillos niger*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip in terms of mg/cm² needed for 99% control of the fungus ($ED_{99}$). The effectiveness of the compounds tested for fungicidal activity is reported in Table II in terms of the percent of the $ED_{99}$ of the test compound of the $ED_{99}$ of the standard Difolatan ®.

Example I

Algae and Aquatic Weeds Control

Representative compounds of the invention were tested as aquatic herbicides and algicides by the following method. The weed test species were *Lemna minor* and *Elodea canadensis* and the algae used was *Spirulina maxima*.

An acetone solution of the test compound and a small amount of an alkylarylpolyoxyethylene glycol-containing surfactant was prepared. This solution was mixed with a nutrient solution in quantity sufficient to give a concentration of 2 ppm. Eight oz. plastic cups were filled with 150 ml of this solution. A sample of the test, Lemna and Elodea, was added together to each cup. Forty ml of Spirulina culture with the 2 ppm treatment was placed in 1½ oz. plastic cups or #4 glass vials. The containers were then placed in an illuminated environment and maintained at a temperature of about 20° C. for incubation. The containers were observed periodically for growth (as compared with an untreated check). The effectiveness of the test compound was determined based on a final observation of growth after 7 to 10 days. The results of the test on a 0-to-100 basis—0 indicating no effectiveness and 100 indicating complete effectiveness—are reported in Table III.

TABLE I

Compounds of the formula

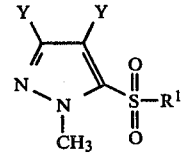

| | | | Elemental Analysis | | | | | |
|---|---|---|---|---|---|---|---|---|
| | | | % C | | % H | | % N | |
| Compound | R¹ | Physical State | Calc. | Found | Calc. | Found | Calc. | Found |
| 1 33349 | —CH₂CH₂Cl | off-white solid | 25.96 | 25.73 | 2.54 | 2.68 | 10.09 | 9.92 |
| 2 35679 | —CH=CH₂ | white solid, mp 66–69° C. | 29.86 | 30.74 | 2.51 | 2.61 | 11.63 | 11.85 |
| 3 38123 | —CH₂CH₂O—S(O)₂CH₃ | white solid | 24.93 | 26.39 | 2.99 | 2.96 | 8.31 | 8.35 |

TABLE II

| | Mycelial Inhibition | | | | | | | | | | |
|---|---|---|---|---|---|---|---|---|---|---|---|
| Compound | Phy. | Rhiz. | Fus. | Botr. | Asper. | GDM | TLB | CLB | TEB | BR | BPM | RB |
| 1 33349 | 0 | 68 | 53 | 43 | 70 | 0 | 0 | 0 | 0 | 0 | 0 | NT |
| 2 35679 | 42 | 56 | 69 | 117 | 156 | 64 | 11 | 0 | 0 | 0 | 0 | NT |
| 3 38123 | 22 | 72 | 54 | 18 | 29 | 75 | 83 | 87 | 0 | 0 | 0 | 100 |

GDM — Grape Downy Mildew (*Plasmopara viticola*)
TLB — Tomato Late Blight (*Phytophthora infestans*)
CLB — Celery Late Blight (*Septoria apii*)
TEB — Tomato Early Blight (*Alternaria solani conidia*)
BR — Bean Rust (*Uromyces phaseoli tipica*)
BPM — Bean Powdery Mildew (*Erysiphe polygoni*)
RB — Rice Blast (*Piricularia oryzae*)

TABLE III

| Compound | Lemna | Elodea | Spirulina |
|---|---|---|---|
| 1 33349 | 75 | 70 | 95 |

TABLE III-continued

| Compound | Lemna | Elodea | Spirulina |
|---|---|---|---|
| 2 35679 | 80 | 70 | 98 |
| 3 38123 | 85 | 70 | 80 |

What is claimed is:

1. A compound of the formula

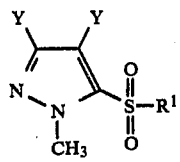

wherein $R^1$ is vinyl, 2-haloethyl, or the group $-CH_2CH_2OS(O)_2CH_3$; and Y is chloro or bromo.

2. A compound according to claim 1 wherein Y is chloro.

3. A compound according to claim 2 wherein $R^1$ is vinyl.

4. A compound according to claim 2 wherein $R^1$ is 2-chloroethyl.

5. A compound according to claim 2 wherein $R^1$ is the group $-CH_2CH_2OS(O)_2CH_3$.

6. A method for controlling fungi which comprises contacting said fungi or their growth environment with a fungicidally effective amount of a compound of the formula defined in claim 1.

7. A method for controlling fungi which comprises contacting said fungi or their growth environment with a fungicidally effective amount of a compound of the formula defined in claim 3.

8. A method for controlling fungi which comprises contacting said fungi or their growth environment with a fungicidally effective amount of a compound of the formula defined in claim 4.

9. A method for controlling fungi which comprises contacting said fungi or their growth environment with a fungicidally effective amount of a compound of the formula defined in claim 5.

10. A fungicidal composition which comprises an inert carrier and a fungicidally effective amount of a compound of claim 1.

11. A fungicidal composition which comprises an inert carrier and a fungicidally effective amount of a compound of claim 3.

12. A fungicidal composition which comprises an inert carrier and a fungicidally effective amount of a compound of claim 4.

13. A fungicidal composition which comprises an inert carrier and a fungicidally effective amount of a compound of claim 5.

* * * * *